United States Patent
Brajnovic et al.

(10) Patent No.: US 7,942,668 B2
(45) Date of Patent: May 17, 2011

(54) DRILL TEMPLATE ARRANGEMENT

(75) Inventors: Izidor Brajnovic, Gothenburg (SE); Andreas Pettersson, Gothenburg (SE)

(73) Assignee: Nobel Biocare Services AG, Zurich-Flughafen (CH)

( * ) Notice: Subject to any disclaimer, the term of this patent is extended or adjusted under 35 U.S.C. 154(b) by 570 days.

(21) Appl. No.: 11/916,262

(22) PCT Filed: May 5, 2006

(86) PCT No.: PCT/SE2006/000541
§ 371 (c)(1),
(2), (4) Date: Nov. 30, 2007

(87) PCT Pub. No.: WO2006/130067
PCT Pub. Date: Dec. 7, 2006

(65) Prior Publication Data
US 2009/0325122 A1 Dec. 31, 2009

(30) Foreign Application Priority Data
Jun. 3, 2005 (SE) ........................ 0501285

(51) Int. Cl.
*A61C 1/08* (2006.01)
(52) U.S. Cl. ........................... 433/76; 433/75
(58) Field of Classification Search ............. 433/75, 433/76, 173, 215
See application file for complete search history.

(56) References Cited

U.S. PATENT DOCUMENTS

| | | | | |
|---|---|---|---|---|
| 5,320,529 A * | 6/1994 | Pompa | ................. | 433/76 |
| 5,362,236 A * | 11/1994 | Branemark | ................. | 433/173 |
| 5,564,926 A * | 10/1996 | Br.ang.nemark | ............ | 433/174 |
| 5,743,916 A | 4/1998 | Greenberg et al. | | |
| 5,967,777 A * | 10/1999 | Klein et al. | ..................... | 433/75 |
| 5,989,025 A | 11/1999 | Conley | | |
| 2005/0170311 A1 * | 8/2005 | Tardieu et al. | .................. | 433/76 |
| 2010/0009314 A1 * | 1/2010 | Tardieu et al. | ................. | 433/144 |

OTHER PUBLICATIONS

International Search Report received in corresponding PCT Application No. PCT/SE2006/000541, mailed Sep. 25, 2006.

* cited by examiner

*Primary Examiner* — Ralph A Lewis
(74) *Attorney, Agent, or Firm* — Knobbe Martin Olson & Bear, LLP

(57) ABSTRACT

A drilling assembly is provided for drilling a hole into a zygoma of a patient. The assembly can comprise a template, an extension unit, a drill guide unit, and first and second drills. The template can be configured for orientation within a patient's mouth and can comprise a guide sleeve having a longitudinal axis extending towards the zygoma when fitted on the patient. The extension unit can include a central bore and be slideably received within the guide sleeve. The drill guide unit can also include a central bore of a different diameter than that of the extension unit. The first drill can be slideably received within the central bore of the guide sleeve. The second drill can have an outer diameter different than that of the first drill and can be configured to be slideably received with the central bore of the drill guide unit.

17 Claims, 3 Drawing Sheets

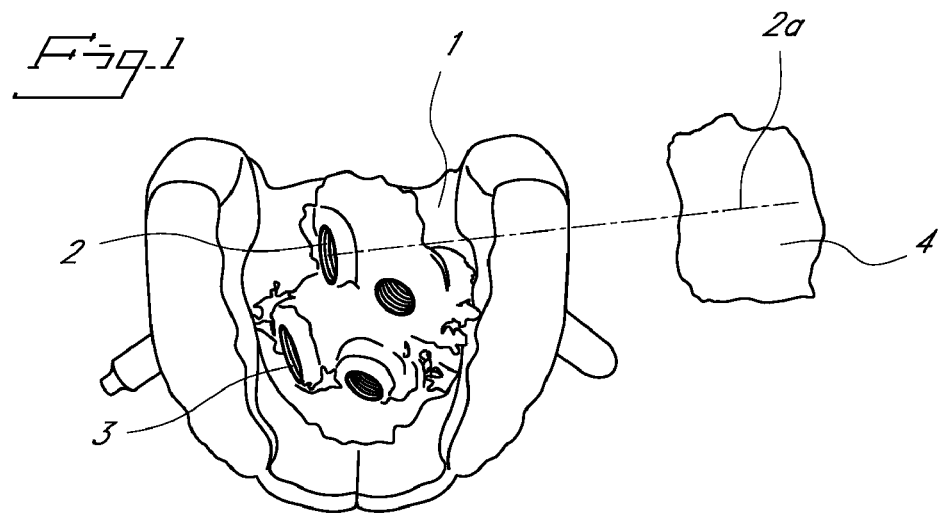
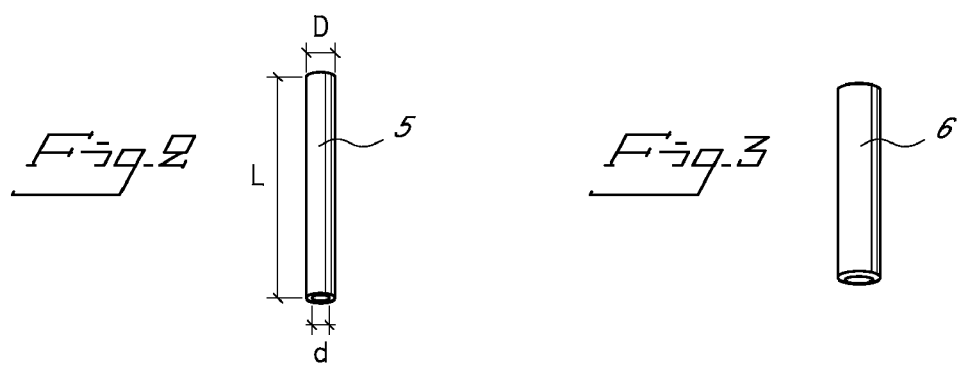
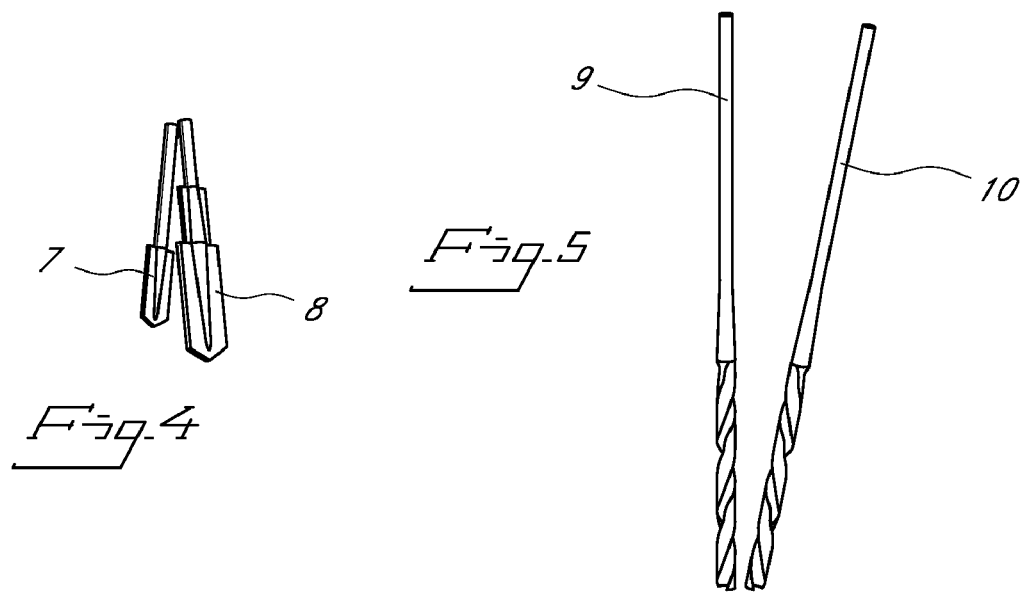

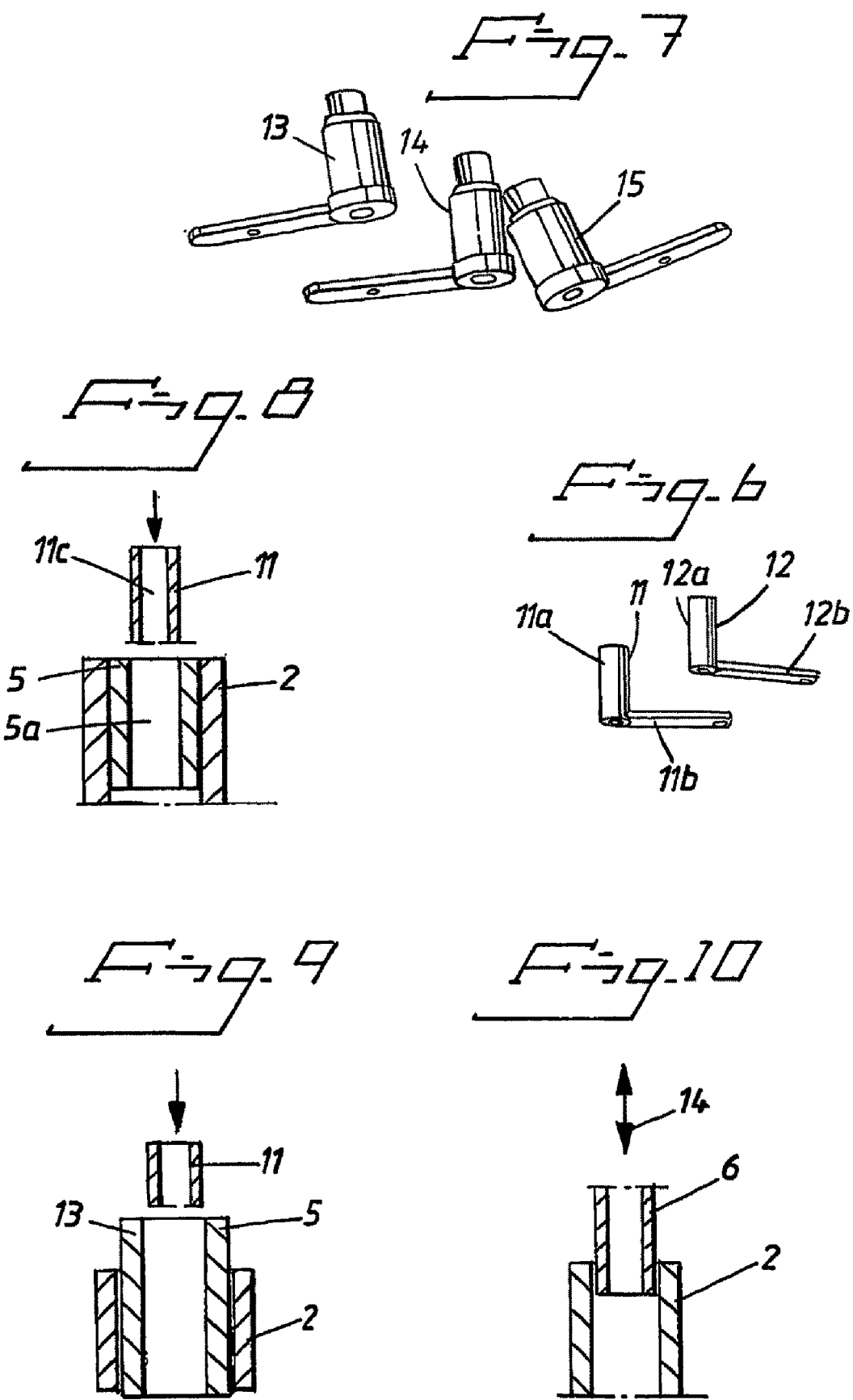

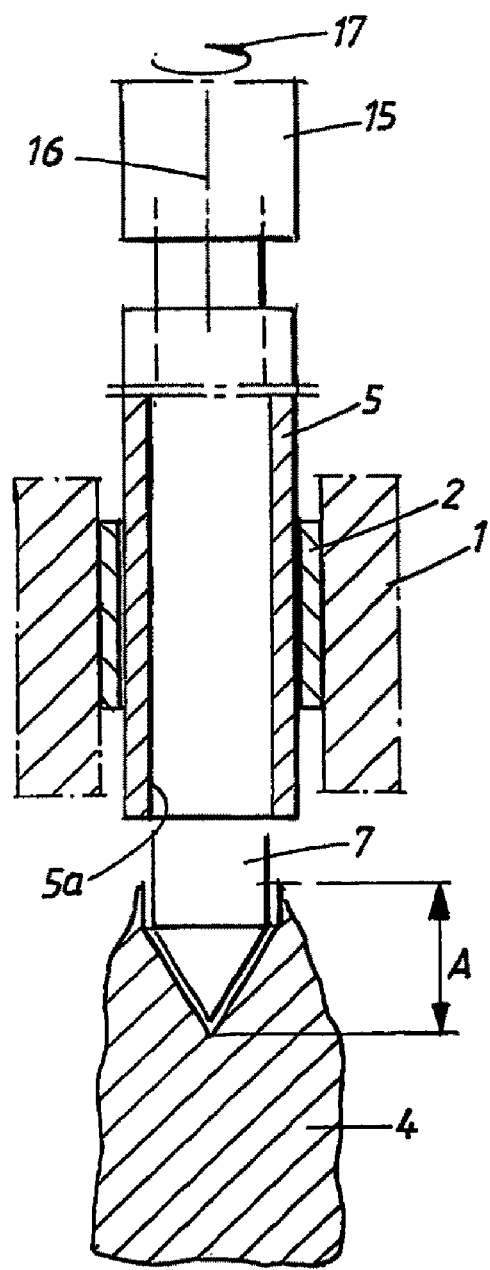
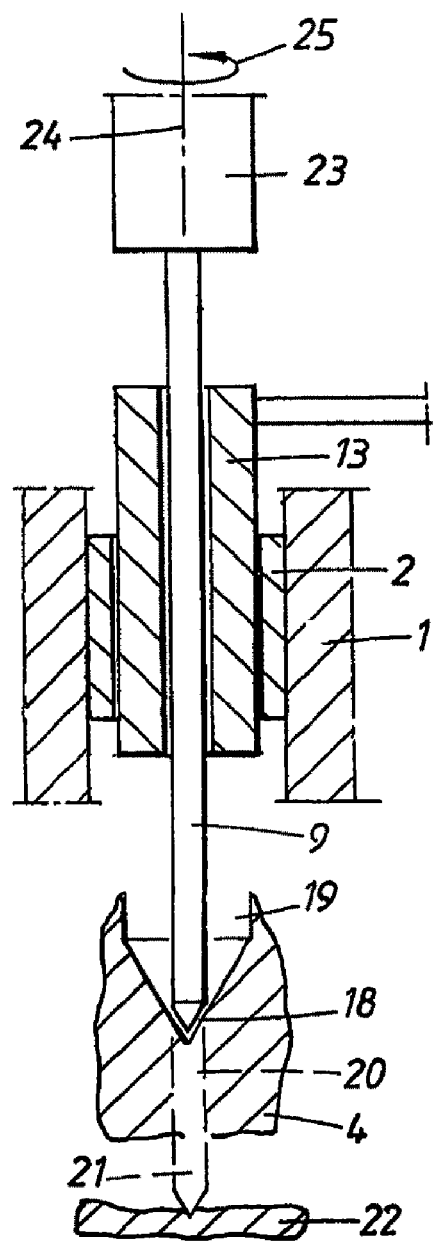

DRILL TEMPLATE ARRANGEMENT

PRIORITY INFORMATION

This application is a U.S. National Phase of International Application No. PCT/SE2006/000541, filed May 5, 2006, which claims priority to Swedish Patent Application No. SE 0501285-1, filed Jun. 3, 2005, each of which is hereby incorporated by reference in its entirety.

BACKGROUND

1. Field of the Invention

The present invention relates to an arrangement used on a drill template oriented in the mouth for forming holes intended to extend from the template and into the zygoma. The template in this case can comprise one or more guide sleeves which define the direction toward the zygoma.

2. Description of the Related Art

Various guide arrangements for guiding drills are already known in dentistry. Special care must be taken when forming holes for implants and screws which are to extend into and be anchored in the zygoma.

SUMMARY OF THE INVENTION

According to at least one of the embodiments herein is the realization that special problems may arise on account of the precision requirements that have to be met in terms of the hole direction when forming holes for implants and screws which are to extend into and be anchored in the zygoma. Incorrect handling and incorrect equipment can mean deviations from the drill direction defined with precision in the computer-aided equipment, which means there may be a high risk of the drill direction being wrong and of the drill penetrating through sensitive parts of the eye or orbital cavity.

The structure and orientation of the drill template is dealt with in a parallel application which was submitted on the same day as the present application and by the same applicant. The drill template is produced, inter alia, by means of computer-aided equipment in a manner known per se.

Embodiments of the present inventions aim to solve these problems, among others. In accordance with some embodiments is the realization that it is also important that, despite the aforementioned precision, the arrangement for hole formation can be highly flexible and that components known per se can be used. The embodiments of the present inventions also deal with this problem.

In accordance with an embodiment, one or more first cylindrical extension units can be used to determine hole direction. These units can be applied in a respective guide sleeve. One or more first drills with one or more first diameters can be directed by means of the respective extension unit toward the jaw bone and/or zygoma in said direction for forming an introductory hole extent with a respective first diameter. Finally, one or more drill guide units for one or more second drills with one or more second diameters can be inserted toward the bottom of the introductory hole extent for continued drilling.

In further embodiments, the first cylindrical extension units can be formed as cylinders with longitudinal and continuous central holes. The extension units can be two in number and can have different diameters for the holes. The drill guide units can be designed with cylindrical portions which have external diameters corresponding to the internal diameters in the respective guide sleeve and/or extension unit. The drill guide units can be designed with handle parts, which can make them easier to maneuver by hand. First drill guide units can be arranged to support second drill guide units in the same way as they themselves are supported in the guide sleeves.

The use of these embodiments can make it possible to achieve an efficient arrangement in which the risks of damage can be effectively avoided.

BRIEF DESCRIPTION OF THE DRAWINGS

The abovementioned and other features of the inventions disclosed herein are described below with reference to the drawings of the preferred embodiments. The illustrated embodiments are intended to illustrate, but not to limit the inventions. The drawings contain the following figures:

FIG. 1 is a bottom perspective view of a drill template which has been produced using computer-aided equipment and which has been assigned an orientation in the patient's mouth, according to an embodiment.

FIG. 2 is a side view of a first extension unit according to an embodiment.

FIG. 3 is a side view of a second vertical unit according to an embodiment.

FIG. 4 is a side view of exemplary drills having first diameters.

FIG. 5 is a side view of exemplary drill bits that can be used in forming holes according to some embodiments.

FIG. 6 is a side perspective view of first drill guide units that can cooperate with guide sleeves of the drill template illustrated in FIG. 1, according to an embodiment.

FIG. 7 is a side perspective view of second drill guide units that can be applied in guide sleeves of the drill template illustrated in FIG. 1 and/or in the first drill guide units illustrated in FIG. 2 or 3, according to an embodiment.

FIG. 8 is a cross-sectional side view of a first drill guide unit arranged in an extension unit applied in a guide sleeve in the drill template, according to an embodiment.

FIG. 9 is a cross-sectional side view of a first drill guide unit arranged in a guide sleeve in a drill template, and a second guide unit that can be applied to the first drill guide applied in the guide sleeve, according to another embodiment.

FIG. 10 is a cross-sectional side view of an extension unit applied to a guide sleeve in the drill template, according to yet another embodiment.

FIG. 11 is a cross-sectional side view of a drill template to the zygoma and the application of an extension unit in the guide sleeve, and also a drill with a first diameter, by means of which an introductory hole extent can be formed, according to an embodiment.

FIG. 12 is a cross-sectional side view of a drill guide unit applied in the guide sleeve of the drill template and guiding a drill down to the bottom of an introductory hole extent for formation of a hole through the zygoma, according to yet another embodiment.

DETAILED DESCRIPTION OF THE PREFERRED EMBODIMENTS

In FIG. 1, a drill template is indicated by 1. The drill template has guide sleeves 2, 3 which are applied with the aid of computer-aided equipment (not shown). The longitudinal axes of the guide sleeves, for example, a longitudinal axis 2a of the guide sleeve 2, are directed toward a solid part of a symbolically indicated zygoma 4. In the present case, the template has two guide sleeves which are directed toward said zygoma part 4 on one side of the zygoma. A corresponding arrangement with two guide sleeves can be present for alignment with the other side of the zygoma.

FIG. 2 shows a cylindrical extension unit 5 from the side. The cylindrical unit 5 has an external diameter D and an internal diameter d and is thus provided with an internal central hole (not shown in FIG. 2) extending in the longitudinal direction of the cylinder. The unit 5 has a length L. In some embodiments, the length can be approximately 30 mm. The diameter D can be approximately 6 mm, and the internal diameter d can be approximately 4 mm. Said unit 5 can be applied to the respective guide sleeve 2, 3 which has an internal diameter slightly greater than the diameter D, i.e. the extension unit 5 can be inserted into the guide sleeve.

FIG. 3 shows an extension unit 6 with in principle the same structure as the unit 5 in FIG. 2. The unit 6 has a structure corresponding to the unit 5 but has different dimensions. In one illustrative embodiment, the unit 6 can be applied in the sleeve 2 or 3 and can receive the sleeve 5 in its longitudinal and continuous central recess. Alternatively, the units 5 and 6 are exchangeable in said sleeve 2 or 3.

FIG. 4 shows two drills 7, 8 known per se. The drill 7 can have a smaller external diameter than the drill 8 and can cooperate with the unit 5 according to FIG. 2, while the drill 8 can cooperate with the unit 6 according to FIG. 3.

FIG. 5 shows two conventional drills 9 and 10. The drill 9 can have a diameter of 2.9 mm and the drill 10 can have a diameter of 3.5 mm. These drill diameters can be substantially less than the drill diameters of the drills 7 and 8 according to FIG. 4.

FIG. 6 shows exemplary embodiments of drill guide units 11 and 12 with cylinder parts 11a and 12a via which the drill guide units can be applied in either the units 5, 6 or, in an alternative embodiment, directly in the guide sleeve 2 in the drill template. The units 11 and 12 also comprise handle parts 11b and 12b by means of which the units can be applied in the central hole in question and which allow the units to be turned about the longitudinal axes of the parts 11a and 12a.

FIG. 7 shows exemplary embodiments of second drill guide units 13, 14, 15 with a corresponding structure to that of the drill guide units 11 and 12, but with different dimensions. In one illustrative embodiment, the units 13, 14 and 15 can be applied directly to the guide sleeve (e.g. guide sleeve 2) in the drill template. It is also conceivable to arrange these guide units 13, 14, and 15 so that they can be applied to the extension units 5 and 6. In one embodiment, the guide units 13, 14, 15 can also receive the guide units 11 and 12 via their longitudinal central holes.

FIG. 8 shows the guide sleeve 2 according to FIG. 1 in diagrammatic form. An extension unit, for example the extension unit 5, is applied in the guide sleeve 2. Thereafter, a guide unit 11 (cf. FIG. 6) can be inserted in the continuous central hole or recess 5a of the extension unit 5 via its guide part 11a. The unit 11 is provided with a longitudinal continuous recess 11c for a drill according to FIG. 5.

FIG. 9 shows another embodiment in which the unit 13 according to FIG. 7 is inserted into the guide sleeve 2 in the drill template according to FIG. 1 and the unit 11 is in turn inserted in the central hole of the unit 13. It should be noted here that the guiding between the different components (the sleeve parts) is considerable and that the gap between two respective units is of the order of magnitude of 0.1 mm.

FIG. 10 shows, in a diagrammatic representation, the insertion of the unit 6 in the direction of arrow 14 into the sleeve 2 in the drill template.

FIG. 11 shows a hole being formed in connection with the sleeve 2 in the template 1 where the extension unit 5 is applied in the guide sleeve. The unit 5 guides a drill 7 (or 8) via its longitudinal central hole 5a. By means of the drill, an introductory hole extent is formed in the solid part of the zygoma 4. The introductory extent has the length A and can be varied from case to case. The drill is driven by mechanical equipment (electric motor) 15 of a type known per se and in a manner known per se. The equipment 15 rotates the drill about its longitudinal axis 16, for example in the drilling direction 17.

FIG. 12 is intended to show the stage where the hole formation is completed following the state shown in FIG. 11. The extension unit 5 has been replaced here by the drill guide unit 13 (see FIG. 7) which assumes the position shown in FIG. 12 in the guide sleeve 2 of the drill template 1. In this case, the drill 9 according to FIG. 5 is used, which drill can thus be guided by the unit 13 and move to the bottom 18 of the hole 19 formed by the drill 7. The end of the drilled hole 19 is cone-shaped and the drill 9 in this way acquires a locating function. In FIG. 12, the continuation of the hole formed with the drill 9 is indicated by broken lines 20. In the present case, the drill has been allowed to penetrate slightly out of the zygoma 4, with the result that the drill can be felt by the fingers through the patient's skin 22 outside the zygoma.

It will be appreciated that the drill hole formation can be carried out in stages with different drills of different diameters. Thus, the hole 19 can be started with the drill 17 according to FIG. 4 and completed with the drill 8 according to FIG. 4. Correspondingly, the drills 9 and 10 with the different diameters can be used for forming the hole 20. It will also be appreciated that different configurations and dimensions can be used on the drill guide units 11-15. The hole parts 19 and 20 formed can subsequently be threaded with a thread tap (not shown) in a manner known per se. In FIG. 12, the drive equipment for the drill 9 is indicated by 23, which drive equipment can be of the same type as the drive equipment 15 and for example can comprise a drill machine, screwdriver, etc. The longitudinal axis is indicated by 24 in the case according to FIG. 12, while the direction of rotation is indicated by 25.

In accordance with an embodiment, the drill guides 10, 11 according to FIG. 6 can be used on an instrument (not shown) by means of which it is possible to indicate and mark out on the patient's skin outside the zygoma the drill end of the drill which is used for forming the hole 20. Said instrument is described in more detail in an application submitted on the same day as the present application and by the same Applicant as for the present patent application. Said instrument is designed with a sleeve-shaped fastening or anchoring part which can extend in the guide sleeve in the drill template. Each of said units 10, 11 can thus be inserted by way of its cylindrical part into the sleeve of the instrument and the precision or play between the parts is of the same order of magnitude as has been described above.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

The invention claimed is:

1. A method of for drilling a hole into a zygoma of a patient, the method comprising:
   applying a template comprising a guide sleeve to a patient;
   slideably inserting an extension unit into the guide sleeve;
   slideably inserting a first drill having a first diameter into the guide sleeve;
   forming an introductory hole;
   slideably inserting a drill guide unit into the template;
   slideably inserting a second drill having a second diameter smaller than the first diameter of the first drill into the drill guide unit;
   locating a bottom end of the introductory hole with a tip of the second drill to guide the second drill at two points using the drill guide unit and the bottom end of the introductory hole in a locating function; and
   forming a continuation hole into a solid part of the zygoma with the second drill until the drill penetrates the zygoma and with the continuation hole being generally coaxially aligned with the introductory hole.

2. The method of claim 1, wherein the drill guide unit is slideably inserted into the guide sleeve.

3. The method of claim 1, wherein the drill guide unit is slideably inserted into the extension unit.

4. The method of claim 3, wherein the extension unit and the drill guide unit are each generally cylindrical.

5. The method of claim 1, wherein the steps of slideably inserting a first drill into the guide sleeve, forming an introductory hole into a solid part of the zygoma with the first drill, slideably inserting a drill guide unit into the template, slideably inserting a second drill with a smaller diameter than the first drill into the drill guide unit, and forming a continuation hole into the solid part of the zygoma with the second drill until the drill penetrates the zygoma are repeated within a second guide sleeve of the template and with the continuation hole being generally coaxially aligned with the introductory hole.

6. The method of claim 5, further comprising using a second extension unit to form a second introductory hole, each of the extension units having central bores of different diameters.

7. The method of claim 1, further comprising sliding the drill guide unit relative to the extension unit in a longitudinal direction.

8. The method of claim 7, further comprising slideably inserting the drill guide unit within a central bore of the extension unit.

9. The method of claim 1, further comprising aligning a longitudinal axis of the extension unit with a longitudinal axis of the guide sleeve.

10. The method of claim 9, further comprising aligning a longitudinal axis of the drill guide unit with a longitudinal axis of the extension unit and a longitudinal axis of guide sleeve.

11. The method of claim 1, further comprising maneuvering the drill guide unit using a handle part thereof.

12. The method of claim 11, wherein the handle part has a longitudinal axis that extends perpendicularly relative to a longitudinal axis of a central bore of the drill guide unit.

13. The method of claim 1, further comprising inserting a second drill guide unit within a central bore of the first drill guide unit for receiving the second drill.

14. The method of claim 13, further comprising inserting into the central bore of the second drill guide unit a drill bit having a diameter of between 2.9 mm and 3.5 mm.

15. The method of claim 1, further comprising inserting a second extension unit within a central bore of the first extension unit.

16. The method of claim 1, further comprising forming introductory holes and continuation holes using a template having four guide sleeves, the guide sleeves being disposed in pairs on opposing sides of the template and the guide sleeves each defining a longitudinal axis directed toward the zygoma of the patient.

17. The method of claim 1, further comprising sliding the extension unit relative to the guide sleeve in a longitudinal direction.

* * * * *